United States Patent [19]

Vetter et al.

[11] Patent Number: 5,135,496
[45] Date of Patent: Aug. 4, 1992

[54] TAMPER-PROOF HYPODERMIC SYRINGE ASSEMBLY

[75] Inventors: Helmut Vetter, Ravensburg; Peter Geprägs, Weingarten, both of Fed. Rep. of Germany

[73] Assignee: Arzneimittel GmbH Apotheker Vetter & Co., Ravensburg, Fed. Rep. of Germany

[21] Appl. No.: 524,347

[22] Filed: May 16, 1990

[30] Foreign Application Priority Data

May 17, 1989 [EP] European Pat. Off. ............ 89710045

[51] Int. Cl.$^5$ ............................................. A61M 5/00
[52] U.S. Cl. ..................................... 604/111; 604/199
[58] Field of Search .............. 604/111, 110, 239, 240, 604/241, 242, 243, 905, 192, 197–200; 215/250, 251, 252, 253, 254, 255, 256, 258

[56] References Cited

U.S. PATENT DOCUMENTS

| | | | |
|---|---|---|---|
| 3,485,239 | 11/1967 | Vanderbeck | 604/192 |
| 3,739,779 | 4/1970 | Pfleger | 604/241 |
| 3,820,652 | 6/1974 | Thackston | 604/110 |
| 3,989,044 | 11/1976 | Meierhoefer | 604/192 |
| 4,231,486 | 11/1980 | Bock | 215/250 |
| 4,300,678 | 11/1981 | Gyure | 604/111 |
| 4,493,427 | 1/1985 | Wolkonsky | 215/258 |
| 4,720,285 | 1/1988 | Pickhard | 604/192 |
| 4,747,500 | 5/1988 | Gach | 215/250 |
| 4,781,701 | 11/1988 | Geprägs | 604/240 |

FOREIGN PATENT DOCUMENTS

| | | | |
|---|---|---|---|
| 2503032 | 8/1975 | Fed. Rep. of Germany | 604/111 |
| 0096303 | 7/1960 | Netherlands | 604/200 |
| 725024 | 3/1955 | United Kingdom | 604/240 |

*Primary Examiner*—C. Fred Rosenbaum
*Assistant Examiner*—Mark Bockelman
*Attorney, Agent, or Firm*—Herbert Dubno

[57] ABSTRACT

A hypodermic syringe assembly has a hollow body having a neck centered on an axis, an elastomeric plug fitted in the neck and having an end projecting axially forward from the neck, a stiffening sleeve fitted over the plug and neck and having a collar fitting around the projecting plug end and itself projecting axially therepast, an elastomeric stopper fitted into the collar, and a protective cap fitted over the plug, sleeve, and stopper. A destructible connection between the cap and the sleeve retains the cap in place on the body over the plug, sleeve, and stopper. This cap is therefore only removable from the body by destruction of the connection. The protective cap is basically cylindrical and centered on the axis and has a front end wall generally transverse of the axis and an opposite rear end edge and the destructible connection extends annularly between the end edge of the cap and the sleeve. Furthermore the destructible connection includes a ring fixed on the sleeve and having a front end edge confronting the rear end edge of the cap and the connections itself is between the end edges.

10 Claims, 2 Drawing Sheets

TAMPER-PROOF HYPODERMIC SYRINGE ASSEMBLY

FIELD OF THE INVENTION

The present invention relates to a hypodermic syringe. More particularly this invention concerns a tamperproof body for such a syringe.

BACKGROUND OF THE INVENTION

A standard hypodermic syringe comprises a bottle having a neck normally fitted with a plug that in turn is formed with an axially throughgoing passage that may be blocked by a thin frangible membrane. A stiffening sleeve formed of a synthetic resin somewhat stiffer than that of the plug fits over the neck and plug and forms a forwardly projecting collar to which the hub of the needle cannula when the device is used. A stopper can be fitted in and/or over the collar to maintain sterility.

With such an arrangement, unless it is provided in a sealed package, it is impossible to know if the interior of the bottle is sterile, whether or not it already contains some injectable medication. Even if a package is provided, once it is opened it is impossible to tell if the interior of the bottle remains sterile.

OBJECTS OF THE INVENTION

It is therefore an object of the present invention to provide an improved hypodermic syringe assembly.

Another object is the provision of such an improved hypodermic syringe assembly which overcomes the above-given disadvantages, that is which, even if not provided in a hermetic package, gives a clear indication if it has been opened or otherwise tampered with.

SUMMARY OF THE INVENTION

A hypodermic syringe assembly according to this invention has a hollow body having a neck centered on an axis, an elastomeric plug fitted in the neck and having an end projecting axially forward from the neck, a stiffening sleeve fitted over the plug and neck and having a collar fitting around the projecting plug end and itself projecting axially therepast, an elastomeric stopper fitted into the collar, and a protective cap fitted over the plug, sleeve, and stopper. A destructible connection between the cap and the sleeve retains the cap in place on the body over the plug, sleeve, and stopper, This cap is therefore only removable from the body by destruction of the connection.

With this arrangement, therefore, the cap, which is constructed so that it will not fit snugly or hold on the sleeve unless the destructible connection is intact, will give the user clear indication whether the package has been tampered with. The cap will cover any parts that need to remain sterile, so that if it is in place, the hypodermic can be used.

According to another feature of this invention the protective cap is basically cylindrical and centered on the axis and has a front end wall generally transverse of the axis and an opposite rear end edge and the destructible connection extends annularly between the end edge of the cap and the sleeve. The destructible connection includes a ring fixed on the sleeve and having a front end edge confronting the rear end edge of the cap and the connection itself is between the end edges. The destructible connection can be a thin web unitarily and integrally formed with the ring and cap and interconnecting the end edges thereof. It can also be constituted as a radially open groove formed on one of the end edges and a barb ring formed on the other end edge and engaging radially in the groove.

In accordance with further features of the invention the ring and sleeve are formed with radially interfitting formations that are substantially stronger than the destructible connection. These formations include a radially projecting annular ridge and a radially open annular groove receiving the ridge. Furthermore, the front end wall of the cap is formed at the axis with an axially throughgoing aperture substantially smaller than the stopper. Thus the user can ascertain if the stopper is in place, but cannot remove it through the aperture. The front end wall of the cap axially rearwardly engages the stopper to hold it in place, and the sleeve and collar taper axially forward.

According to this invention a frangible web is unitarily formed with and interconnects the rear end edge of the ring and the front end of the sleeve. Thus the assembly can be put together simply by driving the cap and ring back over the sleeve so as first to rupture the frangible web, then to push the ring back into place on the sleeve, locking it on the bottle neck. This feature is particularly convenient when the sleeve has a split skirt that can be spread to fit over the neck of the bottle. The ring is thus pushed home to lock the fingers formed by the split skirt in place and to thereby lock the sleeve in place on the bottle.

DESCRIPTION OF THE DRAWINGS

The above and other objects, features, and advantages will become more readily apparent from the following, reference being made to the accompanying drawing in which.

SPECIFIC DESCRIPTION

Figure 1:
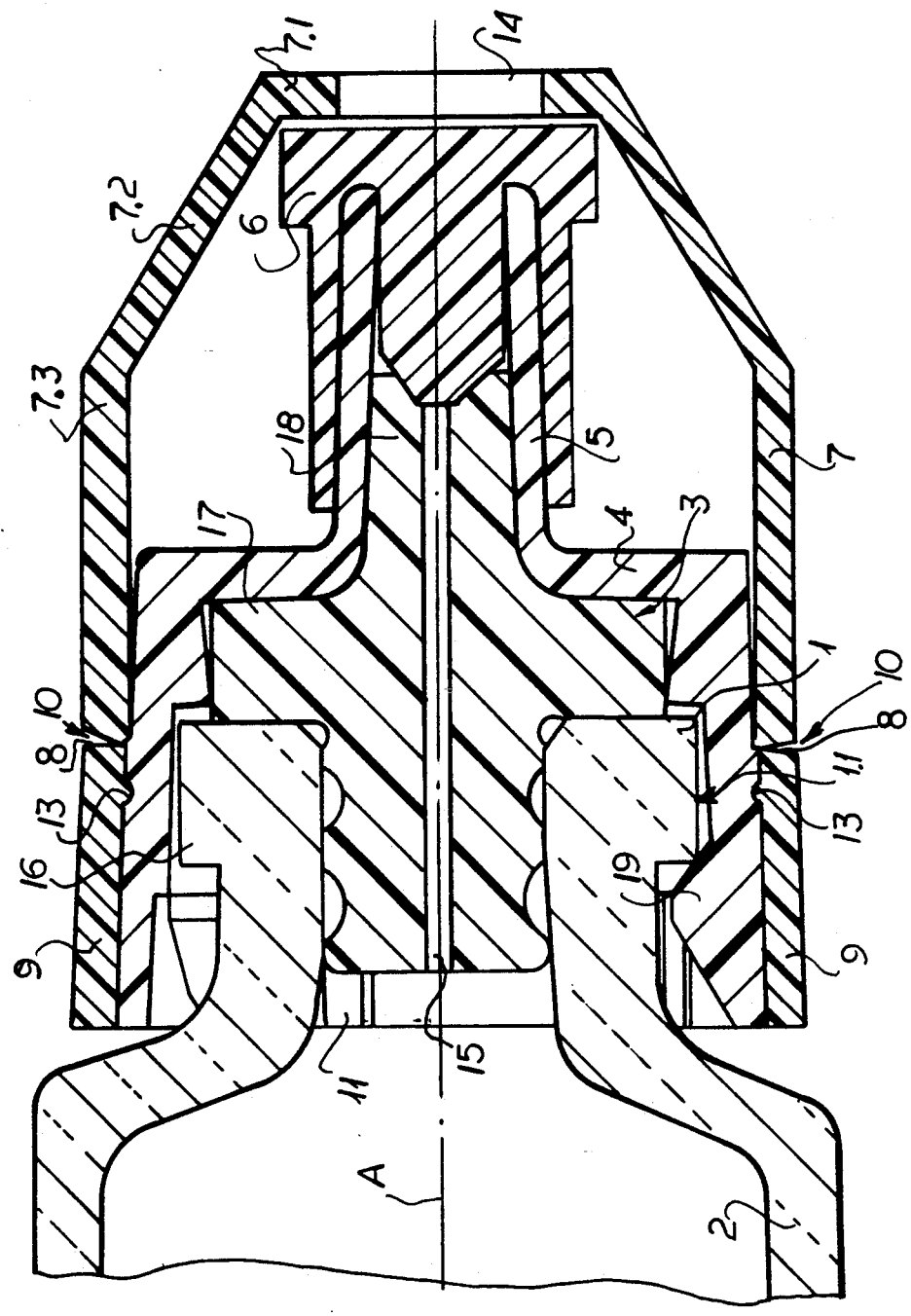
FIG. 1 is an axial section through the front end of a hypodermic assembly according to this invention.

As seen in FIG. 1 a hypodermic according to this invention basically comprises a synthetic-resin or glass body or bottle 2 having at its front end a neck 1 centered on an axis A and having a radially outwardly projecting rim 16. A soft elastomeric plug 3 is fitted into this neck 1 and is formed on the axis A with an axially throughgoing cylindrical passage 15 to which is fitted an unillustrated needle cannula as is well known per se.

The plug 3 itself has a flange 17 that sits on the axial front face of the neck 1 and is formed with a small-diameter axial extension 18. A somewhat stiffer protective sleeve 4 centered on the axis A fits over the neck 1 and plug 3 and has a forwardly tapering collar 5 snugly surrounding the projection 18 and extending axially forward somewhat past it. The sleeve 4 is formed with a basically cylindrical split skirt 11 having bumps 19 that engage behind the rim 16 to lock it tightly in place on the neck 1. The hub of the unillustrated needle cannula fits over this collar 5 when the needle itself is engaged in the passage 15. A soft elastomeric stopper 6 in turn is fitted over the collar 5. Thus the package can be delivered sterile and, if desired, already filled with a medication.

According to this invention a protective cap 7 is provided which has a transverse end wall 7.1 joined via a frustoconical wall 7.2 to a cylindrical side wall or skirt 7.3. The end wall 7.1 is formed centered on the axis A with a circular throughgoing hole 14 of smaller outside diameter than the plug 6 so that the presence of this plug 6 can be checked but it cannot be removed through the hole 14. The rear end of the side wall 7.3 is joined at a destructible connection 10 to a ring 9 that fits snugly on the sleeve 4. A ridge 13 formed on this ring 9 fits in a complementary groove formed in the sleeve 4 so that these two parts, which taper identically, are a very tight fit together. The ring 9 is annularly continuous so that once it is fitted over the split skirt 11 of the sleeve 4 it locks same very solidly on the neck 1. The rear face of the end wall 7.1 bears on the front end of the stopper 6 to hold it in place also.

The destructible connection 10 here is a thin web 8 that is unitarily formed with the cap 7 and ring 9, which both are made of a stiff synthetic resin. The strength of the connection of the ring 9 to the sleeve 4 and in turn of the sleeve 4 to the neck 1 is greater than the strength of the web 8, so that the cap 7 can only be removed by breaking this web 8. In addition the cylindrical inside surface of the skirt 7.3 of the cap 7 is not complementary to the frustoconical outer surface of the sleeve 4 so that, once the web 8 is broken, the cap 7 will not fit or hold on the sleeve 4. This web 8 therefore forms a connection 10 that will surely indicate if the cap 7 has been tampered with in that, if tampered with, the cap 7 will not stay on the assembly. Nonetheless once intentionally removed, the stopper 6 will protect the sterility of the critical front regions of the assembly.

Figure 2:
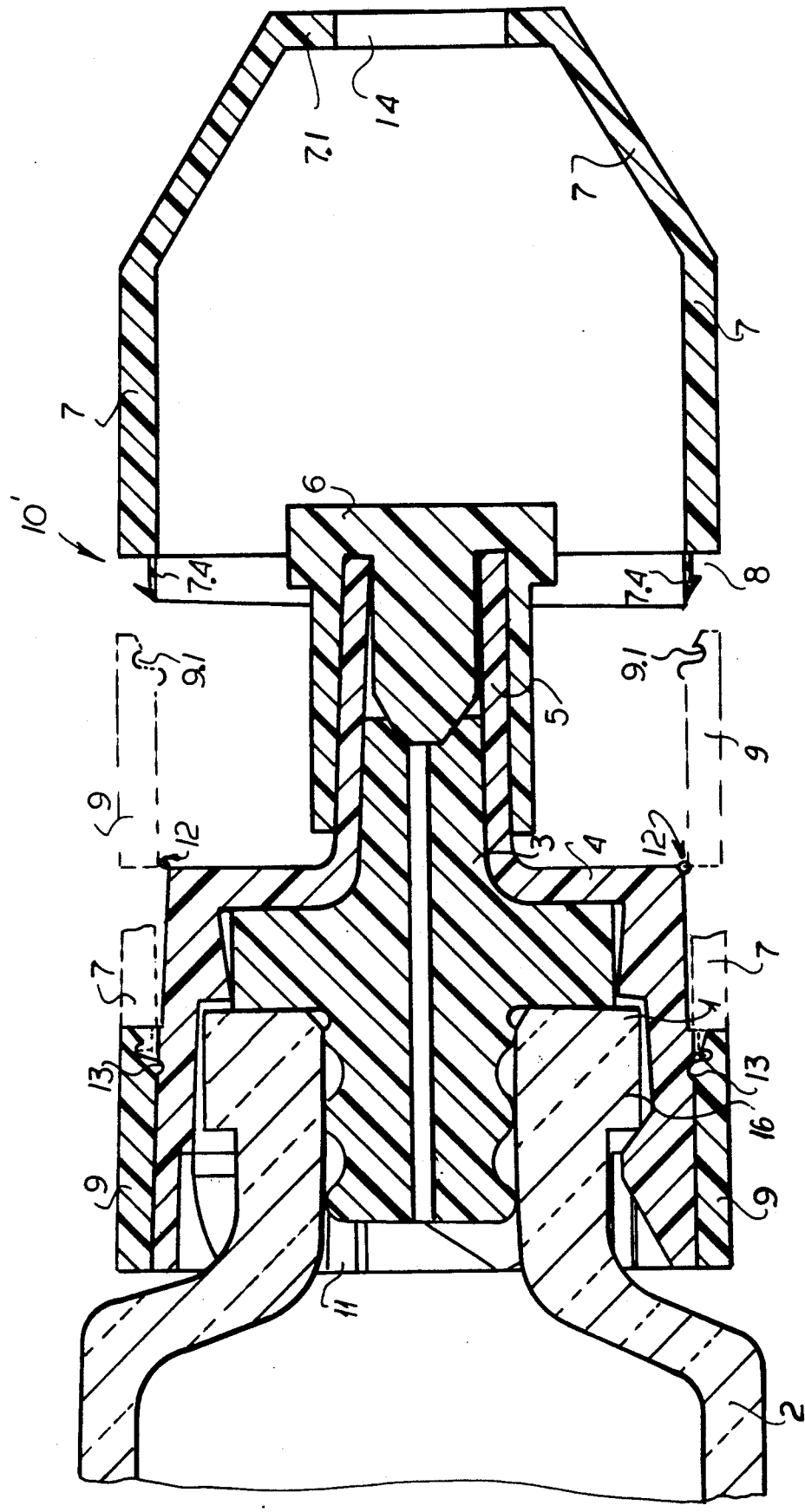
FIG. 2 is a view like FIG. 1 of another arrangement in accordance with the present invention with positions during assembly shown in dashed lines.

In FIG. 2, where references identical to those of FIG. 1 are used for functionally identical structure, the connection 10 is replaced by a connection 10' constituted as a basically L-section lip or barb 7.4 formed at the rear end edge of the cap 7 and a radially inwardly open groove 9.1 formed at the front end edge of the ring 9, immediately forward of the ridge 13. The barb 7.4 can be snapped into the groove 9.1, but will break if pulled axially forward therefrom.

Furthermore FIG. 2 shows in dashed lines how the inside periphery of the rear end of the ring 9 is connected by a frangible web 12 to the front end edge of the sleeve 4. Thus the sleeve 4 carrying the ring 9 is fitted over the neck 1 and the cap 7 is pushed back on it, thereby snapping the barb 7.4 into the groove 9.1, breaking the web 12, and forcing the ring 9 back onto the sleeve 4 so its ridge 13 fits into the groove of the sleeve 4.

We claim:

1. A hypodermic syringe assembly comprising:
    a hollow body having a neck centered on an axis;
    an elastomeric plug fitted in the neck and having an end projecting axially forward from the neck;
    a stiffening sleeve fitted over the plug and neck and having a collar fitting around the projecting plug end and itself projecting axially forward therepast;
    an elastomeric stopper fitted into the collar;
    a protective cap fitted over the sleeve and stopper and having a rear end edge;
    a ring fixed on the sleeve and having a front end edge confronting the rear end edge of the cap;
    means including a destructible connection between the rear end edge of the cap and the front end edge of the ring for retaining the cap in place on the body over the plug, sleeve, and stopper, the cap only being removable from the body by destruction of the connection, the destructible connection comprising
    a radially open groove formed on one of the end edges and
    a a barb ring formed on the other end side and engaging radially in the groove; and
    means including interfitting formations on the body, sleeve, and ring, the engagement of said formations fixing the sleeve on the body and the ring on the sleeve and said formations establishing connections between the ring, sleeve and body that are substantially stronger than the destructible connection.

2. The hypodermic syringe assembly defined in claim 1 wherein the protective cap is basically cylindrical and centered on the axis and has a front end wall generally transverse of the axis, the destructible connection extending annularly between the rear end edge of the cap and the front end edge of the ring.

3. The hypodermic syringe assembly defined in claim 2 wherein the front end wall is formed at the axis with an axially throughgoing aperture of a diameter substantially smaller than a diameter of the stopper.

4. The hypodermic syringe assembly defined in claim 3 wherein the front end wall axially rearwardly engages the stopper.

5. A hypodermic syringe assembly comprising:
    a hollow body having a neck centered on an axis;
    an elastomeric plug fitted in the neck and having an end projecting axially forward from the neck;
    a stiffening sleeve fitted over the plug and neck and having a collar fitting around the projecting plug end and itself projecting axially forward therepast;
    an elastomeric stopper fitted into the collar;
    a projective cap fitted over the sleeve and stopper and having a rear end edge;
    a ring fixed on the sleeve and having a front end edge confronting the rear end edge of the cap;
    means including a destructible connection between the rear end edge of the cap and the front end edge of the ring for retaining the cap in place on the body over the plug, sleeve, and stopper, the cap only being removable from the body by destruction of the connection; and
    means including interfitting formations on the body, sleeve, and ring, the engagement of said formations fixing the sleeve on the body and the ring on the sleeve and said formations establishing connections between the ring, sleeve and body that are substantially stronger than the destructible connection, the formations including a radially projecting annular ridge on the ring and a radially open annular groove on the sleeve receiving the ridge.

6. A hypodermic syringe assembly comprising:
    a hollow body having a neck centered on an axis;
    an elastomeric plug fitted in the neck and having an end projecting axially forward from the neck;
    a stiffening sleeve fitted over the plug and neck and having a collar fitting around the projecting plug end and itself projecting axially forward therepast, the sleeve and collar tapering axially forward;
    an elastomeric stopper fitted into the collar;
    a projective cap fitted over the sleeve and stopper and having a rear end edge;
    a ring fixed on the sleeve and having a front end edge confronting the rear end edge of the cap;
    means including a destructible connection between the rear end edge of the cap and the front end edge of the ring for retaining the cap in place on the body over the plug, sleeve, and stopper, the cap only being removable from the body by destruction of the connection; and means including interfitting formations on the body, sleeve, and ring, the engagement of said formations fixing the sleeve on the body and the ring on the sleeve and said formations establishing connections between the ring, sleeve and body that are substantially stronger than the destructible connection.

7. The hypodermic syringe assembly defined in claim 6 wherein the destructible connection in a thin web unitarily and integrally formed with the ring and cap and interconnecting the end edges thereof.

8. The hypodermic syringe assembly defined in claim 6 wherein the destructible connection is constituted as a radially open groove formed on one of the end edges and a barb ring formed on the other end edge and engaging radially in the groove.

9. A hypodermic syringe assembly comprising:
a hollow body having a neck centered on an axis;
an elastomeric plug fitted in the neck and having an end projecting axially forward from the neck;
a stiffening sleeve fitted over the plug and neck and having front end formed with an axially forwardly projecting collar fittable around the projecting plug end and itself projecting axially therepast;
an elastomeric stopper fitted into the collar;
a protective cap fittable over the plug, sleeve, and stopper;
a ring centered on the axis, snugly fittable over the sleeve axially rearward on the front end thereof, and having a rear end edge and a front end edge;
a frangible web unitarily formed with an interconnecting the rear end edge of the ring and the front end of the sleeve;
means including a destructible connection between the cap and the ring for retaining the cap on the ring, the cap and ring being displaceable backward over the sleeve with tearing of the web to fit the ring snugly to the sleeve; and
radially interfitting formations that are substantially stronger than the destructible connection and that interconnect the ring and sleeve when the ring is fitted snugly over the sleeve rearward of the front end thereof.

10. The hypodermic syringe assembly defined in claim 9 wherein the formations include a radially outwardly projecting annular rim on the body and a radially inwardly projecting bump on the sleeve receiving the ridge.

* * * * *